United States Patent [19]

Flüge et al.

[11] Patent Number: 5,571,789

[45] Date of Patent: Nov. 5, 1996

[54] USE OF URODILATIN IN PULMONARY AND BRONCHIAL DISEASES

[75] Inventors: Thomas Flüge; Wolf-Georg Forssmann, both of Hannover, Germany

[73] Assignee: Haemopep Pharma GmbH, Germany

[21] Appl. No.: 335,695

[22] PCT Filed: May 12, 1993

[86] PCT No.: PCT/EP93/01189

§ 371 Date: Nov. 15, 1994

§ 102(e) Date: Nov. 15, 1994

[87] PCT Pub. No.: WO93/23070

PCT Pub. Date: Nov. 25, 1993

[30] Foreign Application Priority Data

May 15, 1992 [DE] Germany .................. 42 16 133.9

[51] Int. Cl.$^6$ .................. C07K 1/04; C07K 14/00; A61K 38/02; A61K 37/24

[52] U.S. Cl. ........................... 514/12; 514/21

[58] Field of Search ......................... 514/12, 21

[56] References Cited

FOREIGN PATENT DOCUMENTS 8806596  7/1988  WIPO.
9221332  10/1992  WIPO.

OTHER PUBLICATIONS

Hulks et al, British Medical Journal, vol. 299, 28 Oct. 1989 pp. 1081–1082, "Bronchiodilator Effect of Atrial Natriuretic Peptide in Asthma".

Primary Examiner—Howard E. Schain
Assistant Examiner—P. Lynn Touzeau
Attorney, Agent, or Firm—Nikaido, Marmelstein Murray & Oram LLP

[57] ABSTRACT

The present invention relates to the use of a pharmaceutic composition containing urodilatin as an active substance and optionally pharmaceutically usual diluents, excipients, fillers or adjuvants for treating pulmonary and/or bronchial diseases.

11 Claims, 12 Drawing Sheets

USE OF URODILATIN IN PULMONARY AND BRONCHIAL DISEASES

The present invention relates to the use of the peptide hormone urodilatin for treating pulmonary and/or bronchial diseases.

The use of the peptide hormone urodilatin as a hypotensive agent is known in the field of pharmaceutics (DE 37 06 731.1; DE 37 17 329.4; PCT/EP88/00144).

Obstructive diseases of the air passages are characterized by spasm of the bronchial muscles, swelling of the bronchial mucosa and enhanced production of bronchial secretion in varying intensities. In particular, they comprise bronchial asthma, chronic-obstructive diseases of the air passages (COLD), as well as cardiac asthma. The administration of $\beta_2$-sympathomimetics (e.g. fenoterol, salbutamol, terbutalin) is known as a therapy for obstructive diseases of the air passages. $\beta_2$-sympathomimetics lower the tonus of the smooth bronchial muscles, and in addition they inhibit release of mediator substances from the mast cells and enhance the mucocilious clarifying function. However, long term and/or high dosage use of $\beta_2$-sympathomimetics may result in a desensibilization of $\beta_2$-adrenoceptors and hence in a large reduction of therapeutic effectiveness.

In addition, the bronchodilatory activity of the atrial natriuretic peptide (ANP) with asthma is well known (Hulks et al., Br. Med. J. 299 (1989), 1081–1982).

The object of the present invention is to provide a new therapeutic agent for pulmonary and/or bronchial diseases, in particular obstructive diseases of the air passages, that can be used instead of known therapeutic agents or in combination with these.

The object of the invention is achieved by providing a pharmaceutic composition containing urodilatin as the active substance, and optionally pharmaceutically usual diluents, excipients, fillers or adjuvants for treating pulmonary and/or bronchial diseases.

The pharmaceutic composition is especially useful for treating obstructive diseases of the air passages.

The composition is preferably administered parenterally, especially intravenously (e.g. intravenous injection (as a bolus) or intravenous infusion) or inhalatorily, wherein the preferred dosage is from 5 ng to 1000 μg of urodilatin per kg body weight, from 10 ng to 100 μg urodilatin per kg body weight being especially preferred.

In animal experiments it could be shown that with broncho-constriction caused by inhalation of acetylcholin, parenteral administration of urodilatin leads to an obvious protection which becomes apparent in particular in terms of an improved forced expiration.

Surprisingly, it was discovered then that compared with equimolar doses of atrial natriuretic peptide (ANP) the effect of urodilatin was more than two times greater.

Moreover, intravenous application of urodilatin will increase the glomerular filtration rate, the excretion of water, sodium and chloride without the hypotensive effect observed with a similar dosage of ANP. Thus, especially with subjects having a labile circulation urodilatin provides less side effects. The relaxation of the vascular smooth muscles will result in a hypotensive effect only with higher urodilatin doses.

The lower hypotensive effects of urodilatin should also be an advantage, compared with ANP, in a possible therapy of broncho-constriction. In particular the risk of interactions with other hypotensive drugs in the therapy of bronchial asthma, e.g. theophyllin preparations, appears to be diminished.

The invention will be further illustrated by the following Examples in connection with FIGS. 1 to 12.

EXAMPLE 1

1. Methods

Figure 1:
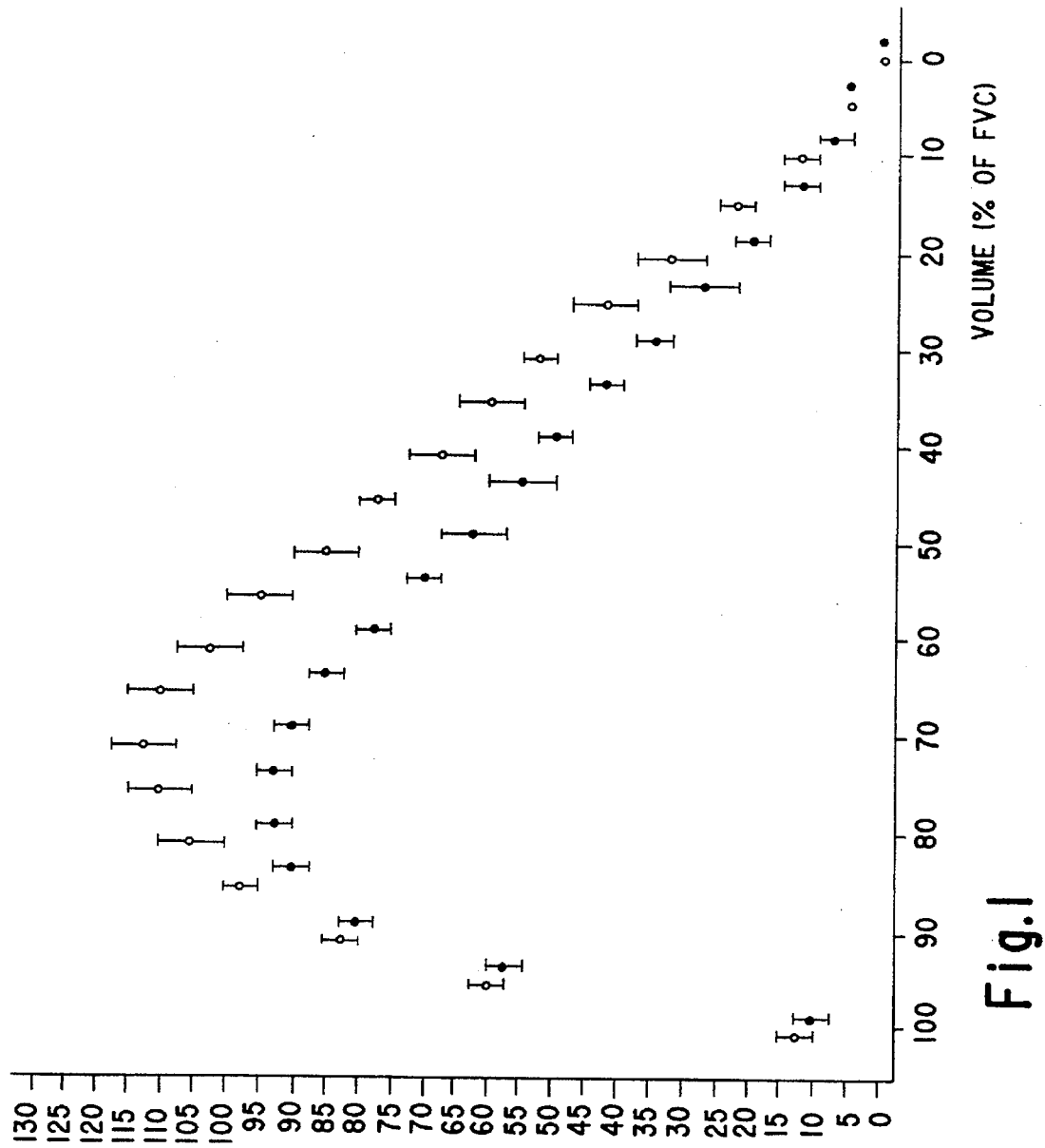
FIG. 1 shows the forced expiratory flow-volume curve at the end of acetylcholin provocation; full circles=control animals, n=7; open circles=group B: 40 ng/kg/min $\Delta$11.4 pmol/kg/min of urodilatin, n=6 (average values ±SEM).

A total of 33 female 12 week wistar rats having body weights of 300 g served as test animals. The design of the study was that of a simple blind approach. On each of the experiment days, animals of the control group and of the verum group were measured.

Employing a test animal body plethysmograph allowed for continuous measurement of the respiration volume (VT), respiration frequency (f), respiration minute volume (MV), resistance of the lung (RL), dynamic compliance (Cdyn), respiration flow (F) and transpulmonary pressure (PTP) of a narcotized, intubated and spontaneously breathing rat. Circulation monitoring was accomplished by EKG recording with evaluation of the heart frequency (HR).

An intravenous entrance (butterfly) was introduced into the caudal vein of the test animals for administration of placebo (NaCl solution) or rerum (urodilatin or ANP in NaCl solution). After steady state conditions were attained the initial values of spontaneous respiration were measured first. Thereafter, a randomized infusion of placebo, urodilatin, or ANP was started. In each case evaluations of the continuously determined spontaneous parameters were made 5 minutes after the beginning of the infusion before an inhalatory acetylcholin (ACh) provocation was made (basic values before Ach provocation).

By means of an injectomar device the test animals were infused 0.5 ml of solution continuously over a total of 10 minutes. The control animals of group A received 0.5 ml NaCl solution, the rats of group B received 40 ng/kg/min= 11.409 pmol/kg/min of urodilatin in NaCl solution corresponding to 120 ng per animal, group C received 80 ng/kg/min=22.819 pmol/kg/min of urodilatin corresponding to 240 ng per animal, and group D received 70.305 ng/kg/min=

22.819 pmol/kg/min of ANP corresponding to 210.915 ng per animal. Thus in groups C and D equimolar doses of urodilatin and ANP were administered. Preliminary experiments where 400 ng/kg/min of urodilatin in a volume of 1 ml were infused showed no changes in heart frequency of the examined animals.

5 minutes after the beginning of the infusion each rat was provoked by inhalation of a defined amount of an ACh aerosol. Evaluation of the spontaneous respiration parameters for each animal was performed after a total inhalation volume of 600 ml (values at the end of ACh provocation).

To complete the experiments, a forced expiration was performed on each animal in hyperventilation induced apnea. Flow-volume and flow-time (spirography) relations were recorded. The flow-volume curve allows for the evaluation of peak expiratory flow (=PEF), maximum mid-expiratory flow (=MMEF), and flow at 75, 50, 25, and 10% of the forced vital capacity (e.g. FEF 75). Spirography of rats primarily yields the forced vital capacity (FVC) and the expired volume after 0.05, 0.10, 0.20 and 0.40 seconds as an absolute value in ml (e.g. FEV 0.05) or in percent of FVC (e.g. FEV 0.05%).

2. Results

2.1 Spontaneous Respiration Parameters

2.1.1 Comparison of the Initial Values for Groups A–D

Measurement of the initial values of F, PTP, VT, Cdyn, RL, f, and MV under spontaneous respiration did not yield any significant differences between groups A–D.

2.1.2 Infusion of NaCl, Urodilatin or ANP 5 minutes after the beginning of the infusion, Group B (40 ng/kg/min of urodilatin) showed a slight, significant increase in PTP and RL and a small, significant decrease of Cdyn as compared to the initial values. In Group C (80 ng/kg/min of urodilatin), a slight, significant decrease in respiration frequency could be seen relative to the initial values. Comparison of all groups among themselves (Anova) and individually with respect to the control group A (t-test) in all resulted in no significant differences between groups A–D for the basic values before ACh provocation and for the percent change thereof after 5 minutes of infusion, based on the initial values (Delta %).

2.1.3 ACh Provocation with Infusion of NaCl, Urodilatin, or ANP

In all groups, ACh provocation resulted in a significant increase in PTP, RL, f, and MV and a significant decrease in VT and Cdyn with respect to the basic values before inhalation. With the exception of group D, all the other groups showed a significant decrease in F. After a total inhalation of 600 ml ACh, comparison of all the measured values and their absolute and relative changes with respect to the basic values before ACh provocation between the groups (Anova) or between each of the individual groups B–D and the control group A (t-test) in all showed no significant changes.

2.2 Forced Expiration

The parameters of forced expiration were measured only at the end of ACh provocation, so a statistic comparison is possible only between groups A–D.

2.2.1 Spirography

The multivariant analysis of variance (Anova) as a comparison within the group and the paired t-test of individual groups B–D with respect to the control group A showed a significant improvement of the expired volume values after 0.05, 0.1, 0.2, and 0.4 seconds (FEV 0.5% etc.), based on the FVC, only for FEV 0.1% in group B (40 ng/kg/min of urodilatin). The other FEV and FEV % values in groups A–D were not significantly distinct.

2.2.3 Flow-volume Curves

Comparison of groups A–D among themselves and individually with respect to the control group A showed a clear improvement of PEF, MNEF, FEF 75, FEF 50, and FEF 25 for groups B (40 ng/kg/min of urodilatin) and C (80 ng/kg/min of urodilatin). The dose of ANP in group D (70.305 ng/kg/min) which was equimolar to that for group C (80 ng/kg/min of urodilatin) caused a significant increase only of PEF and FEF 75 (FIGS. 1 through 3).

Figure 2:
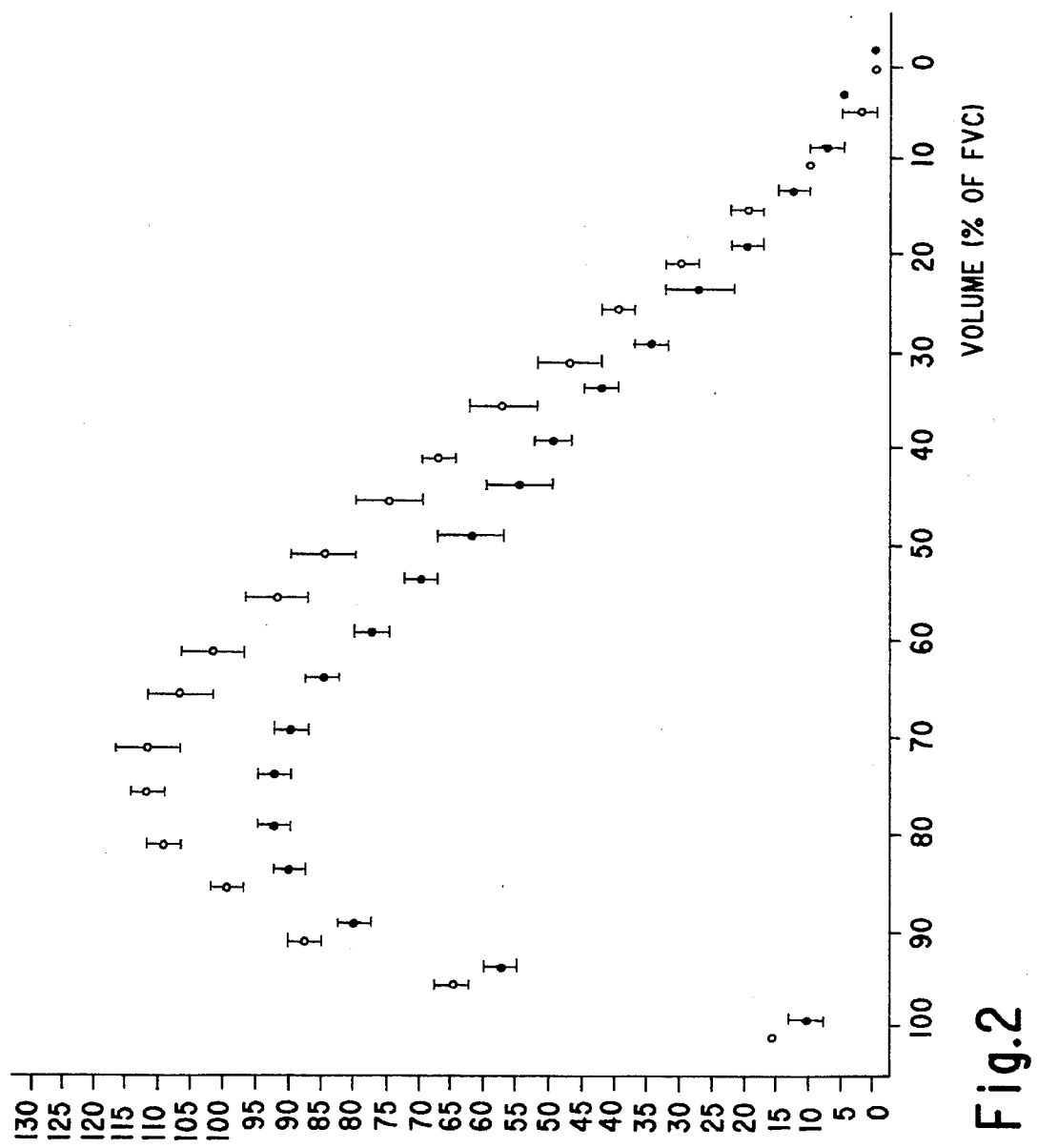
FIG. 2 shows the forced expiratory flow-volume curve at the end of acetylcholin provocation; full circles=control animals, n=7; open circles=group C: 80 ng/kg/min $\Delta$22.8 pmol/kg/min of urodilatin, n=6 (average values ±SEM).
Figure 3:
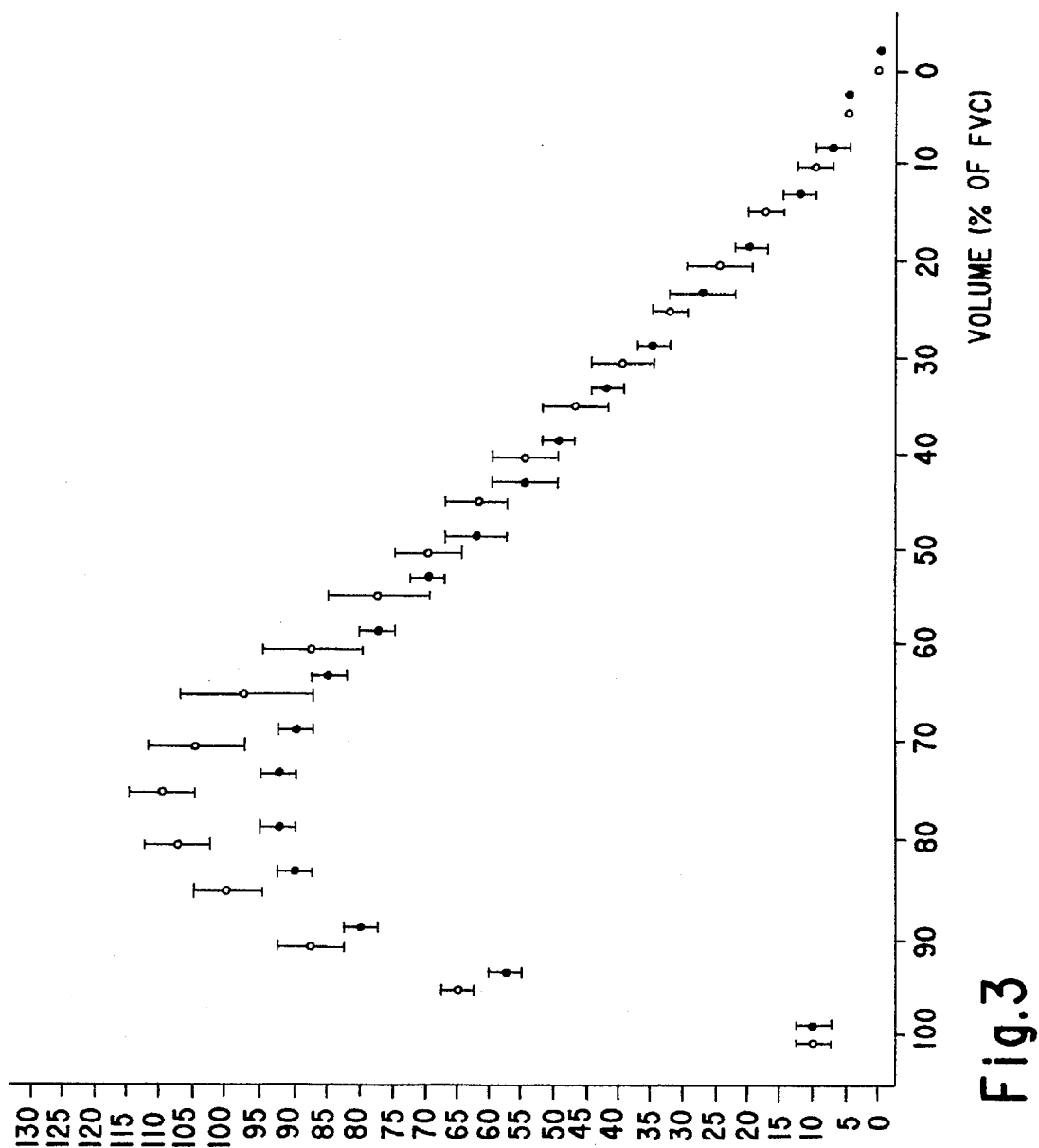
FIG. 3 shows the forced expiratory flow-volume curve at the end of acetylcholin provocation; full circles=control animals, n=7; open circles=group D: 70.3 ng/kg/min $\Delta$22.8 pmol/kg/min of ANP, n=6 (average values ±SEM).

FIGS. 1 to 3 show the forced expiratory flow-volume curve at the end of acetylcholin provocation for groups B (40 ng/kg/min of urodilatin), C (80 ng/kg/min of urodilatin), and D (70.3 ng/kg/min of ANP). From the figures it can be seen that urodilatin (groups B and C) is more effective and acts for a longer period of time than atrial natriuretic peptide (group D). From a comparison of FIGS. 1 and 3 it can be seen that urodilatin at 40 ng/kg/min is clearly more effective than ANP in a (on molar basis) twofold higher dose.

3.3 Heart Frequency

The differences in heart frequency before the beginning of the infusion (initial values), after 5 minutes of infusion (basic values before ACh provocation), and at the end of ACh provocation were not significant between groups A–D.

3. Discussion

3.1 Spontaneous Respiration Parameters

The slight changes in PTP, RL and Cdyn with respect to the initial values upon infusion of 40 ng/kg/min of urodilatin (group B) did not reach any significance in a statistic comparison among the groups and presumably can be considered as consequences of the volume stress caused by the infusion with consequent stiffening of the lung and increase of the air passages resistance from swelling of the bronchial mucosa in the case of especially sensitive animals.

In all groups, ACh provocation resulted in an obvious broncho-constriction with decrease in expansibility of the lung without a significant effect of the urodilatin or ANP infusion on the spontaneous respiration parameters being observed.

3.2 Forced Expiration

Spirography and flow-volume curve are to be considered as sensitive measurement methods for the determination of functional changes in the large central and small peripheral air passages. FEV, FEV %, and PEF reflect the functional condition of the central air passages even better than the resistance determined under spontaneous respiration, whereas the flow measurements at 75, 50, 25, and 10% of the forced vital capacity (FVC) towards smaller lung volumes increasingly reflect the width of the peripheral bronchial tubes. Thus, in spite of the lack of response of the measured spontaneous respiration values, the clearly protective effects of the infusion of 40 and 80 ng/kg/min of urodilatin on the ACh induced changes of the parameters of forced expiration relative to those of control group A which can be observed upon placebo infusion can be considered as significant drug effects. The effects of a dose of 70.305 ng/kg/min of ANP which is equimolar with 80 ng/kg/min of urodilatin were less clearly seen. Even 40 ng/kg/min of urodilatin had a more obvious protective effect than ANP in a twofold higher dosage, on a molar basis. The effect of urodilatin which can be localized predominantly in the peripheral passages may be caused by the nature of the administration as an intravenous infusion.

3.3 Heart Frequency

A significant increase in heart frequency as a consequence of vasodilation upon urodilatin or ANP infusion with reflectory increase of the sympathicotonus could not be detected with the administered doses. Hence, the urodilatin or ANP induced protection from ACh provocation is to be interpreteted as a pharmaceutical effect.

EXAMPLE 2

1. Methods 18 patients of the outpatient bronchial asthma clinic of the *Medizinische Hochschule Hannover*, 2 females and 16 males, aged between 20 and 61 years (33.7±14.8 (average value±STD)) were examined. All of them exhibited mixed-form bronchial asthma, 4 patients additionally suffered from labile hypertension. The anamnesis gave no evidence for an exacerbation of the disease in the last 8 weeks. No nicotine abuse was known from any of the patients. Additional inclusion criteria were defined by an expiratory one-second-capacity ($FEV_{1.0}$) of 40 to 70% of the maximum vital capacity ($VC_{max}$) before administration of a broncho-spasmolytic agent, an effect of a $\beta_2$-sympathomimetic on $FEV_{1.0}$ of $\geq 15\%$, no alteration of the maintenance antiobstructive treatment and no administration of oral corticoids in the last 4 weeks before the beginning of the study. Within 8 hours before the beginning of the examinations no inhalatory application of a $\beta_2$-sympathomimetic must have occurred anymore.

On the day of examination all measurements were made in the period between 9 a.m. and 13 p.m. in order to rule out changes in lung function from circadian variations. First, the fulfilling of the inclusion criteria was documented through a base lung function examination. Determination of the volume-time relationship yielded the measured values for $FEV_{1.0}$ and $VC_{max}$, the flow-volume relationship, the peak expiratory flow (PEF) and the flow at 75, 50, and 25% of the vital capacity ($MEF_{75}$, $MEF_{50}$, $MEF_{25}$=maximum expiratory flow). The physical examination included investigation of the circulation parameters blood pressure and heart frequency. To prevent possible losses of liquid from the diuretic effect of urodilatin, all patients were infused 500 ml of 0.9% saline via an intravenous catheter at the forearm over a period of 30 minutes.

After renewed determination of lung function parameters, blood pressure and heart frequency (pre), infusion of 20, 40, or 60 ng urodilatin per kg body weight per minute (ng/kg/min), corresponding to 5.71, 11.41, or 17.11 pmol/kg/min, was performed over a period of 40 minutes. During this period and over 30 minutes after completion of the infusion the measurements of lung function, blood pressure and heart frequency were repeated in intervals of 10 minutes. In order to document the maximum achievable brochodilatation the patients eventually inhaled 1.25 mg Salbutamol (Sultanol® ready-to-use inhalant). Then, the lung function and circulation parameters were determined anew at the time of maximum subjective effect (Salb).

2. Results

The results are documented by FIGS. 4 through 12. In these figures: *=$p<0.5$ $\Delta$ to pre value; +=$p<0.05$ to 20 ng $\Delta$ to pre value; (in FIG. 12: $p<0.05$ $\Delta$ between dosage groups); ‡=$p<0.05$ to 40 ng $\Delta$ to pre value; #=$\Delta$ uro-max. to Salb n.s. The lung function parameters and the blood pressure values did not show any significant differences between the three dosage groups for the measurement before the beginning of the infusion (pre).

Figure 4:
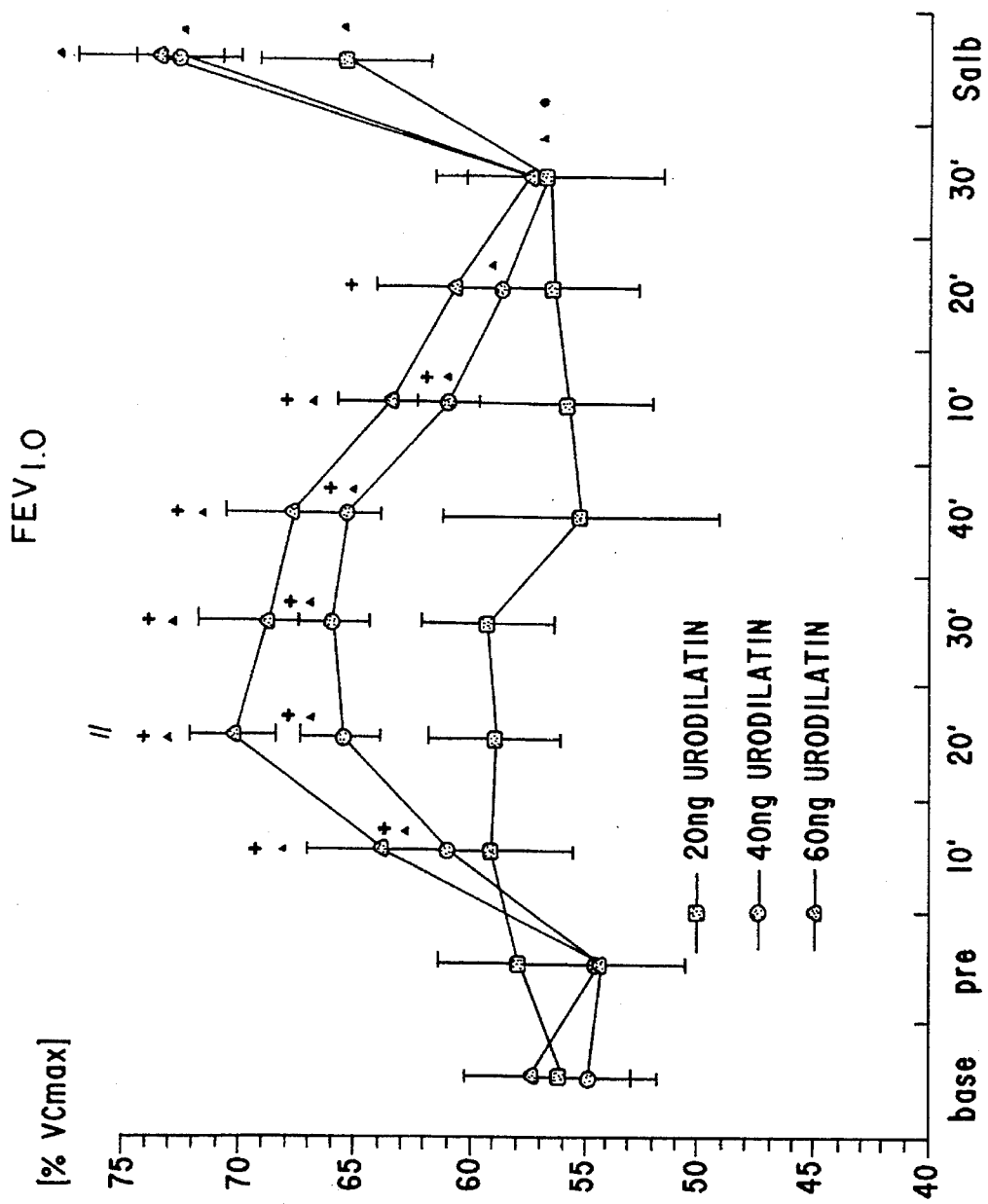
FIG. 4 shows the curve of the expiratory one-second-capacity ($FEV_{1.0}$) in treating a group of patients with infusions of different urodilatin concentrations.
Figure 5:
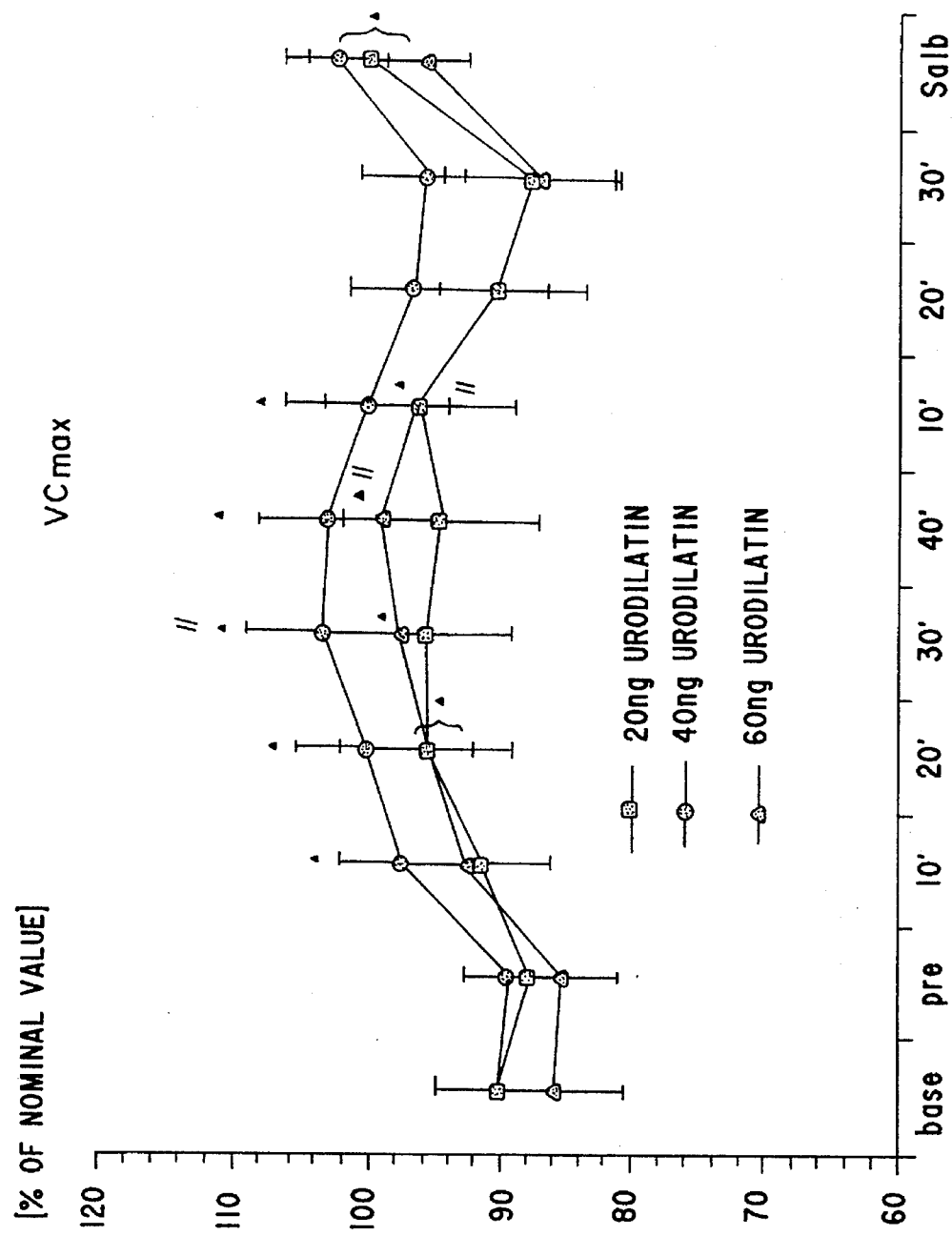
FIG. 5 shows the curve of the vital capacity ($VC_{max}$) in treating a group of patients with urodilatin.
Figure 6:
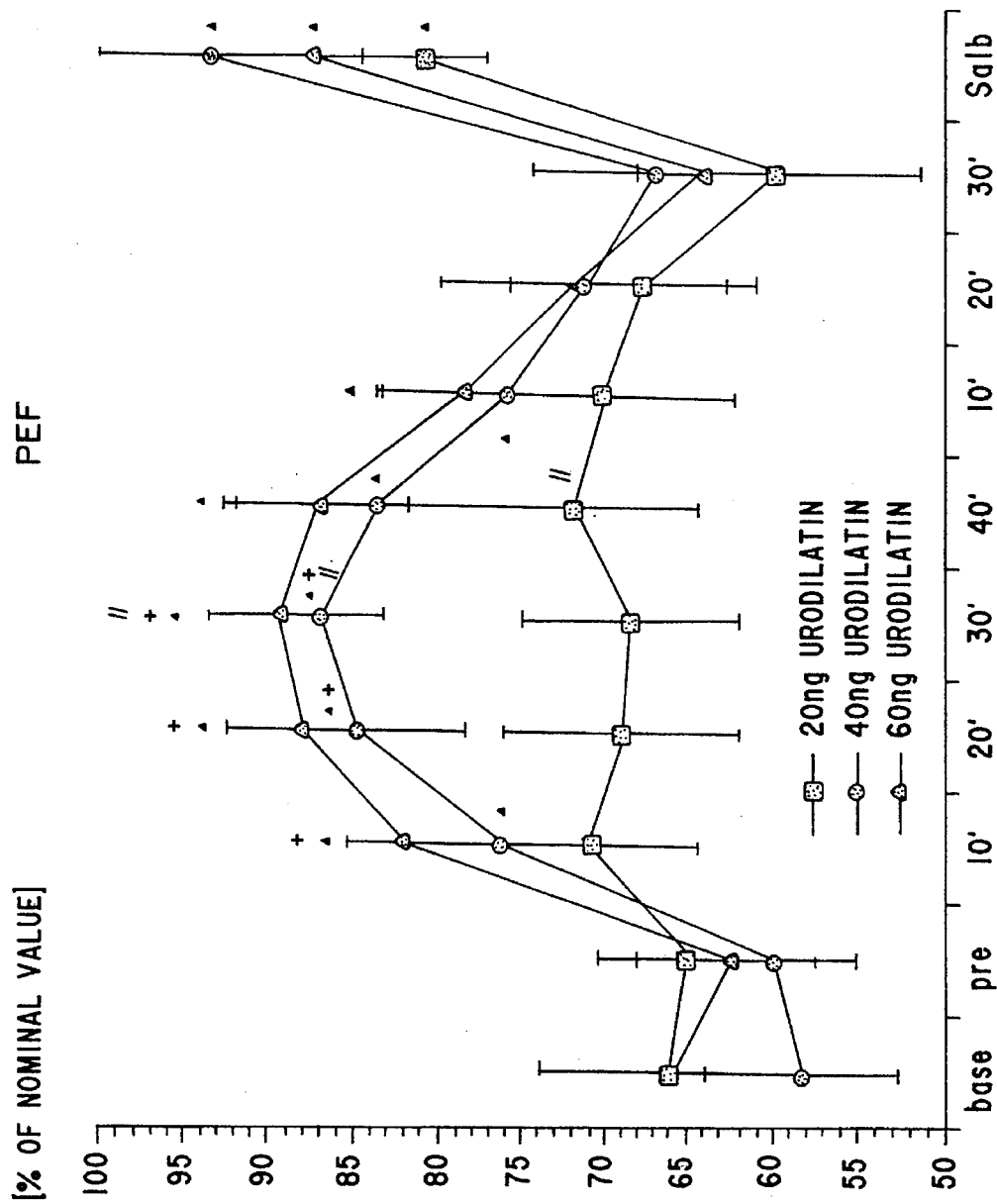
FIG. 6 shows the curve of the peak expiratory flow (PEF) in treating a group of patients with urodilatin.
Figure 7:
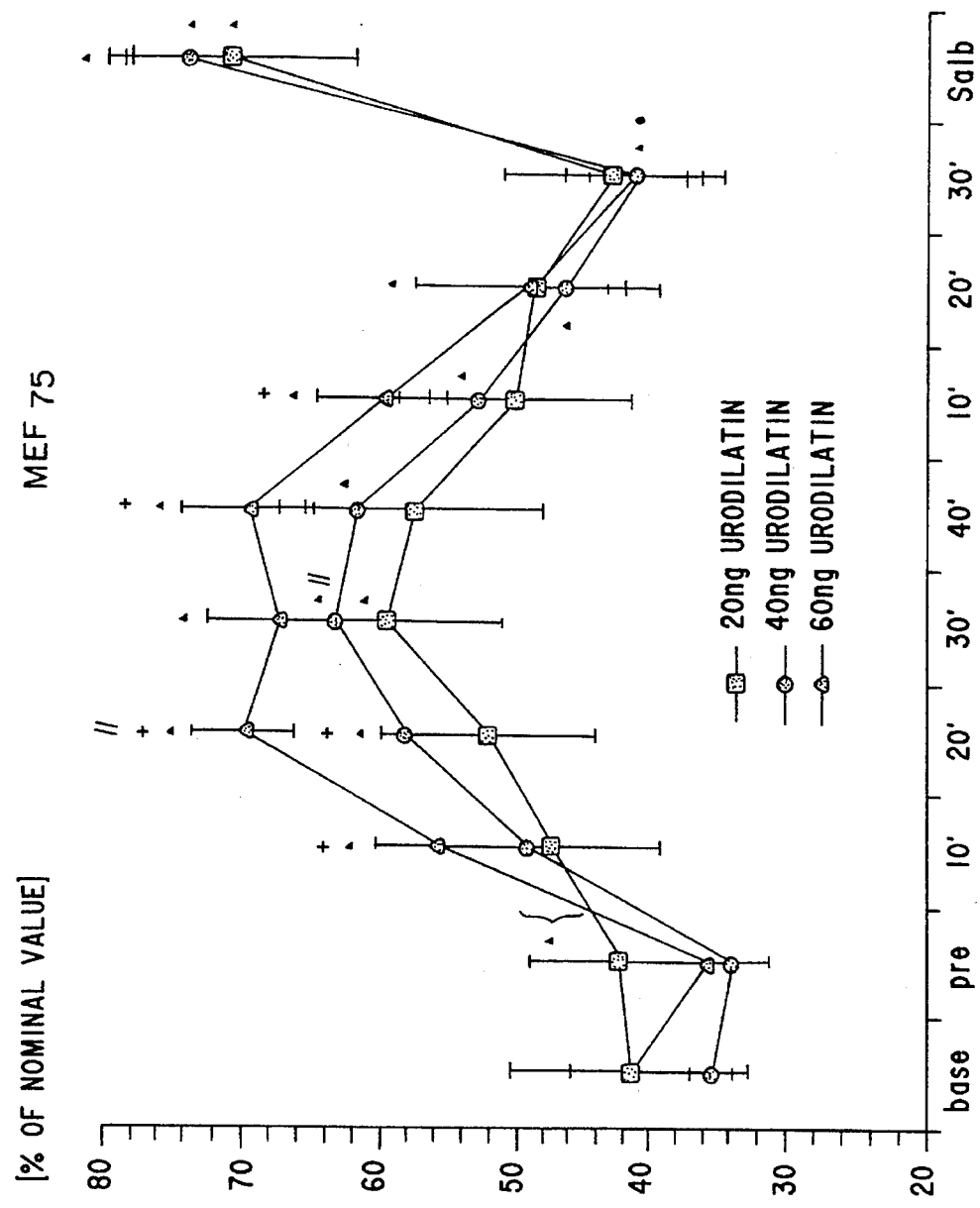
FIGS. 7–9 show curves for the flow at 75, 50 and 25% of vital capacity ($MEF_{75}$, $MEF_{50}$, $MEF_{25}$) in treating a group of patients with urodilatin.
Figure 8:
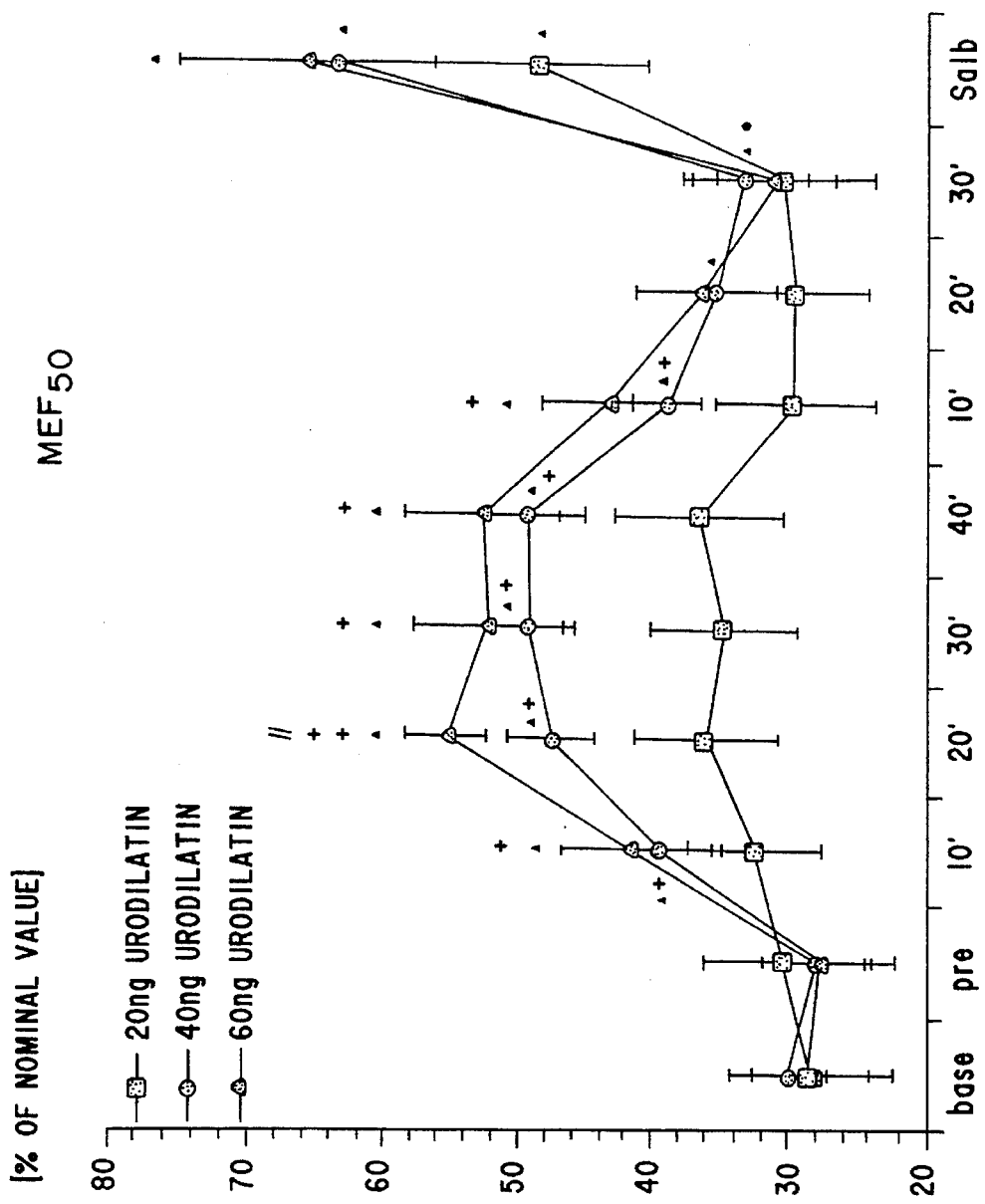
Figure 9:
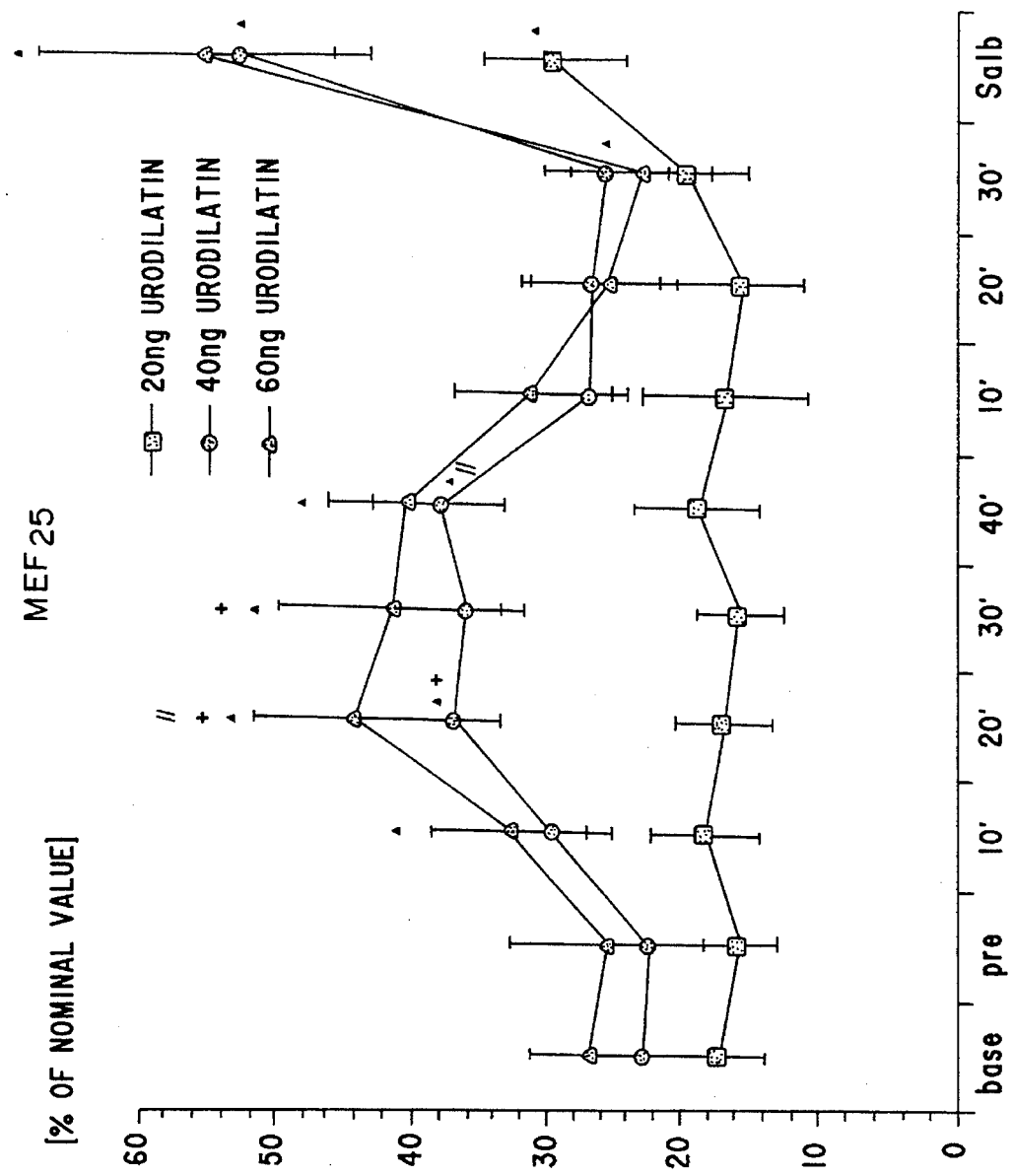

The measurement parameters of the volume-time relationship are depicted in FIGS. 4 and 5. After an infusion period of 10 minutes already, a significant increase of $FEV_{1.0}$ occurred under 40 and 60 ng/kg/min of urodilatin with respect to the pre values and the measurement data of the group 20 ng/kg/min. 20 ng/kg/min of urodilatin did not show any significant effect at any time during or after the infusion. Maximum effect under 60 ng/kg/min of urodilatin occurred after 20 minutes and was no longer significantly different from the measurement values after inhalation of Salbutamol (Salb). The group of patients with the 40 ng/kg/min dosage exhibited the maximum $FEV_{1.0}$ values after 30 minutes of infusion. After completion of the infusion an enhanced drop of the expiratory one-second-capacity occurred so that only the results of the group 40 ng/kg/min were still significantly different from the initial values after 30 minutes. In all three groups, 1.25 mg of Salbutamol resulted in a significant increase in $FEV_{1.0}$.

As a manifestation of the bronchospasmolytic effect of urodilatin, a significant increase of $VC_{max}$ with respect of the pre values could be observed during infusion of 40 and 60 ng/kg/min and until 10 minutes thereafter. The maxima did not show any significant differences from the results after Salbutamol inhalation.

FIGS. 6 through 9 document the course of the measurement parameters of the flow-volume relationship. PEF, $MEF_{75}$, $MEF_{50}$, and $MEF_{25}$ increased during the infusion of 40 and 60 ng/kg/min of urodilatin. Significant differences were reached with respect to the initial values and to the group with 20 ng/kg/min of urodilatin. The maxima under infusion were not significantly different from the measurement results after Salbutamol inhalation, except for $MEF_{50}$ under 40 ng/kg/min. Only the $MEF_{50}$ value after 20 minutes of infusion exhibited a significant difference between 40 and 60 ng/kg/min of urodilatin. 20 ng/kg/min of urodilatin showed an increase of the $MEF_{75}$ measurement value alone reaching an error probability of $p<0.05$ after 10 and 30 minutes of infusion. A significant effect of Salbutamol could be detected in all dosage groups.

Figure 10:
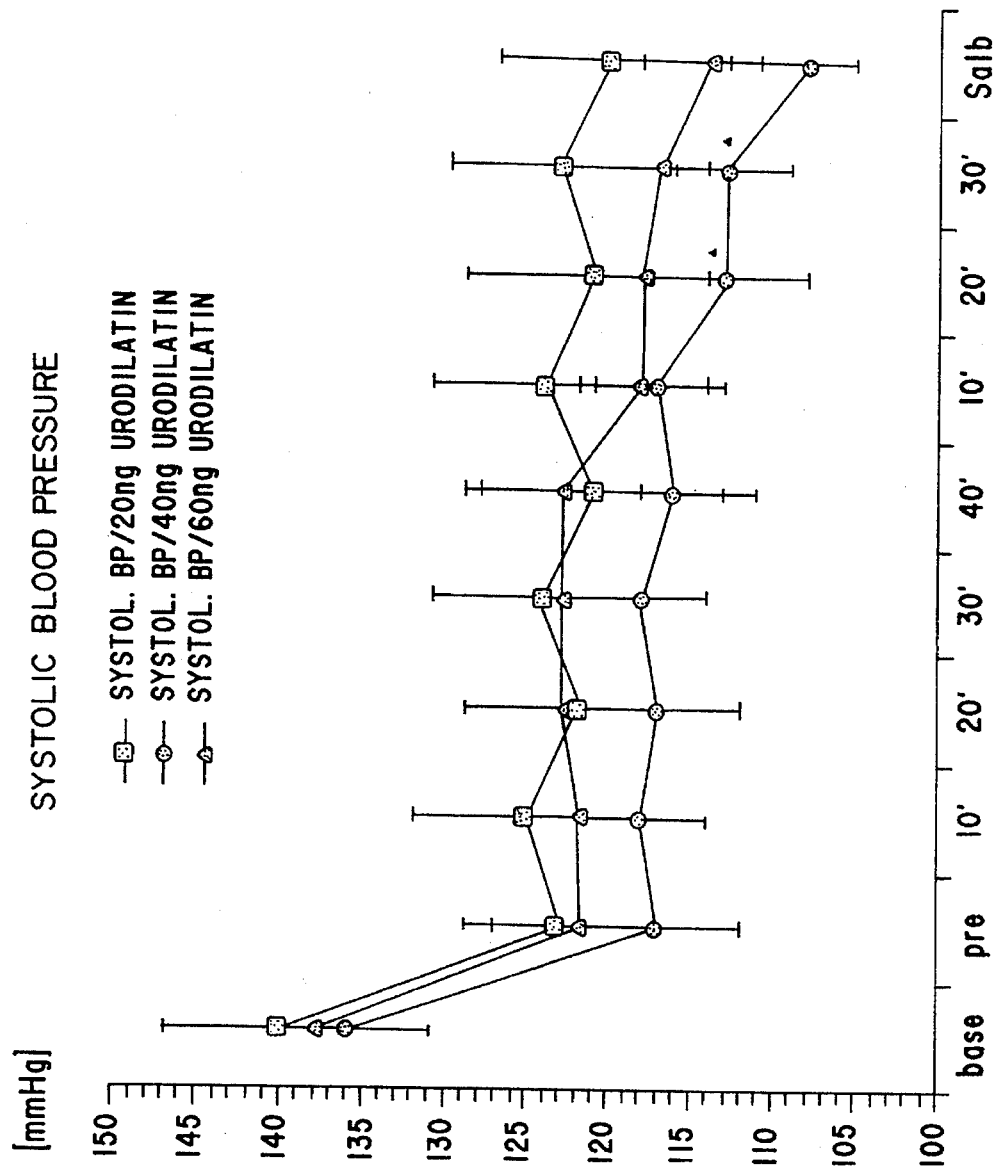
FIG. 10 shows the curve for systolic blood pressure (BP) in mm Hg in treating a group of patients with urodilatin.
Figure 11:
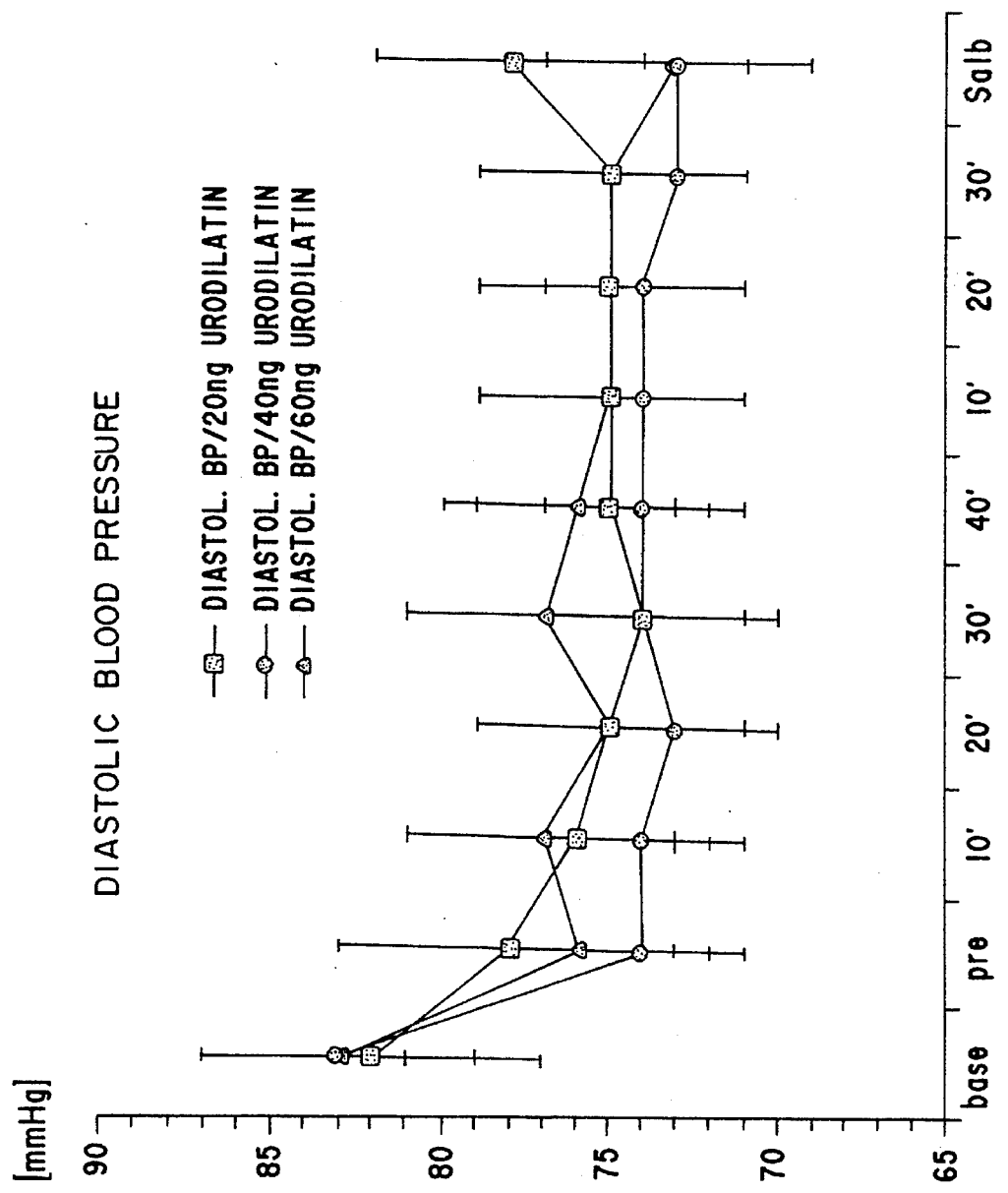
FIG. 11 shows the curve for diastolic blood pressure (BP) in mm Hg in treating a group of patients with urodilatin.
Figure 12:
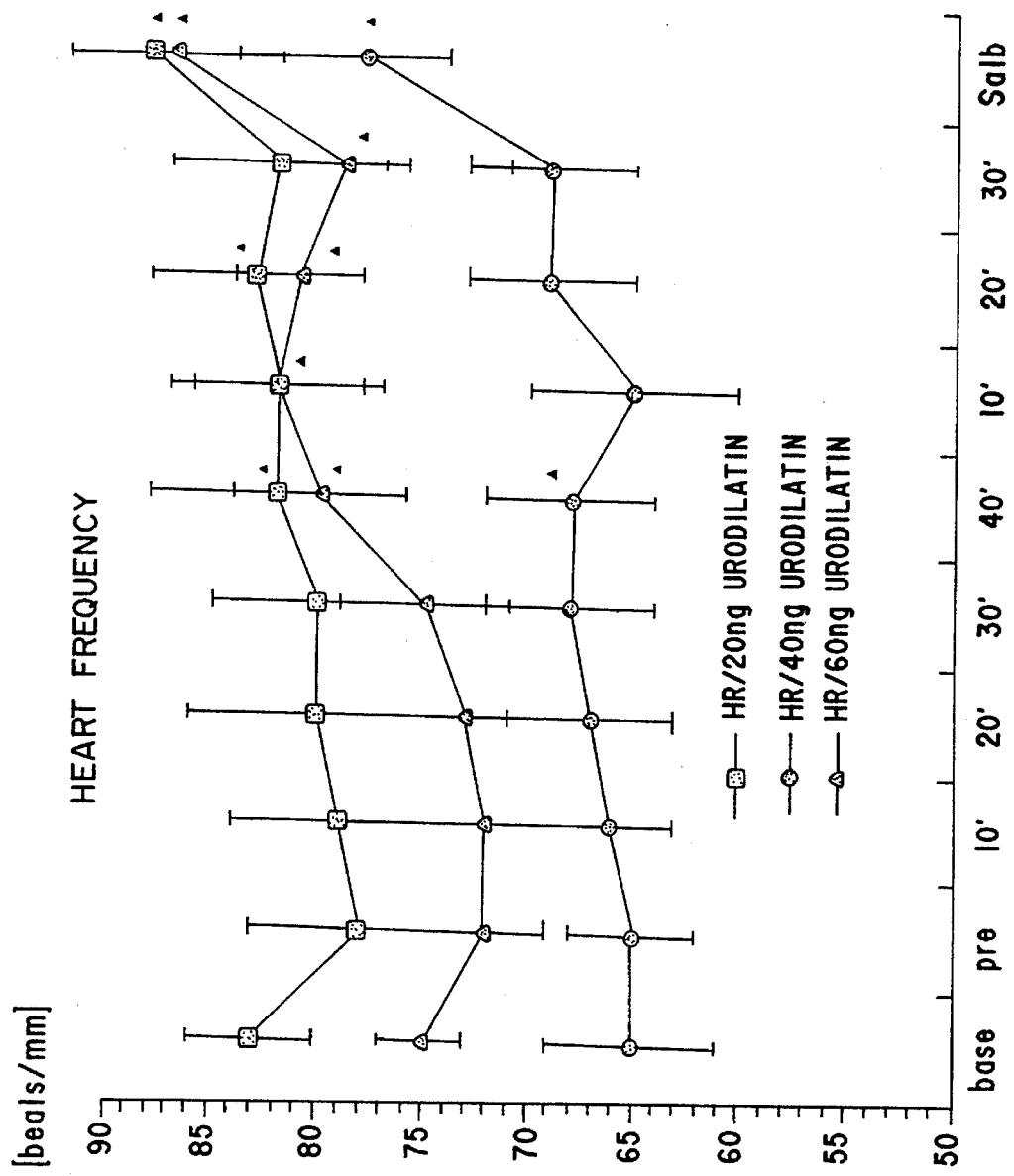
FIG. 12 shows the curve for the heart frequency (HR) in beats/min in treating a group of patients with urodilatin.

FIGS. 10 through 12 depict the course of the circulation parameters. The subsiding of a stress reaction triggered by the physical examination is documented by the reduction of the systolic and diastolic blood pressure values from the base measurement to the determination before the beginning of the infusion. During the infusion no significant change in the blood pressure values occurred in any of the dosage groups. Only 20 and 30 minutes after completion of the infusion of 40 ng/kg/min of urodilatin a significant drop of the systolic blood pressure with respect to the initial values (pre) could be detected.

The heart frequency showed significant differences between the groups already for the base measurement. After 40 minutes of infusion a significant increase with respect to the respective initial values could be detected in all three dosage groups. Only in the group with 60 ng/kg/min of urodilatin, this significant effect endured until 30 minutes after completion of the infusion. After inhalation of 1.25 mg of Salbutamol, a significant increase in heart frequency could be documented for all groups. Average values which were significantly above the urodilatin maxima were reached.

The side effects of urodilatin did not show any correlation with the amount of the infused dose. One patient complained about headaches under 20 ng/kg/min, and with 3 of 18 asthmatics (40 ng/kg/min: 2 patients, 60 ng/kg/min: 1 patient) a transitory bradycardia occurred. A medicamentous intervention was not necessary with any of the patients. With 7 patients (20 ng/kg/min: 2, 40 ng/kg/min: 3, 60 ng/kg/min: 3) a diuretic effect could be observed, whereas 8 of 18 patients (20 ng/kg/min: 3, 40 ng/kg/min: 2, 60 ng/kg/min: 3) did not report any side effects at all.

3. Discussion

Intravenous infusion of 40 and 60 ng/kg/min of urodilatin over a period of 40 minutes did not result in a significant broncho-dilatation with patients having clinically stable bronchial asthma. The increase of PEF, $MEF_{75}$, $MEF_{50}$, and $MEF_{25}$ reflects a predominantly central but also peripheral effect as compared to the values after inhalation of Salbutamol. The possibility ought to be considered that the localization of the bronchodilatory effect could have been affected by the different application types (intravenous/inhalatory).

60 ng/mg/min of urodilatin exhibited even more evidently than 40 ng/kg/min a maximum improvement of the lung function values without significant differences from the results after the inhalation of Salbutamol. On the other hand, 20 minutes after the beginning of the infusion no significant difference between 60 and 40 ng/kg/min could be detected except for $MEF_{50}$. Significant changes in the systolic and diastolic blood pressure values could not be observed during the infusion of the three urodilatin dosages. After 40 minutes of infusion, the heart frequency showed a significant increase in all three groups. Only under 60 ng/kg/min this change could be significantly detected constantly until up to 30 minutes after completion of the infusion. The inhalation of Salbutamol also results in an increase in heart frequency with significantly higher average values as compared to the maxima under urodilatin infusion.

The increase in heart frequency under 60 ng/kg/min must be interpreted as a reflex tachycardia conditioned by the vasodilatory effect of urodilatin. In order to be able to judge the bronchodilatory potential of urodilatin without concomitant indirect effects from an increase of sympathicotonus, a dosage of 40 ng/kg/min corresponding to 11.4 pmol/kg/min should be selected. For direct comparing with ANP and the literature data a dosage of 10 pmol/kg/min of urodilatin would be recommended. Shortening of the infusion time to 30 minutes appears to be possible without significant effects on the achievable urodilatin maxima.

With 7 of 18 subjects, a diuresis was induced by urodilatin. For patients having an uncomplicated bronchial asthma without indications for an insufficiency of the right heart this effect represents a side effect. However, if urodilatin is employed for treating a chronic-obstructive lung disease (COLD) in the course of which a cardioasthenia of the right heart has developed as a consequence of a pulmonary hypertension, the diuresis can be made use of as a desired additional therapeutic effect.

We claim:

1. A method for the treatment of pulmonary or bronchial diseases characterized by spasm of the bronchial muscles, swelling of the bronchial mucosa and enhanced production of bronchial secretion, comprising administering an effective amount of urodilatin to a patient in need of such treatment.

2. The method according to claim 1, wherein said pulmonary or bronchial diseases characterized by spasm of the bronchial muscles, swelling of the bronchial mucosa and enhanced production of bronchial secretion, are obstructive diseases of the air passages.

3. The method according to claim 1, wherein said urodilatin is administered parenterally, intravenously or by inhalation.

4. The method according to claim 1, wherein said urodilatin is administered in a dosage of 5 ng to 1000 µg urodilatin/kg body weight.

5. The method according to claim 4, wherein said urodilatin is administered in a dosage of 10 ng to 100 µg urodilatin/kg body weight.

6. The method according to claim 1, wherein said pulmonary or bronchial diseases are selected from the group consisting of bronchial asthma and chronic obstructive diseases of the air passages.

7. The method according to claim 1, wherein said pulmonary or bronchial diseases are asthma.

8. The method according to claim 1, wherein said bronchial disease is an obstructive bronchial disease.

9. A pharmaceutical composition for the treatment of pulmonary or bronchial diseases characterized by spasm of the bronchial muscles, swelling of the bronchial mucosa and enhanced production of bronchial secretion, comprising an effective amount of urodilatin in combination with a second therapeutic agent for the treatment of obstructive diseases of the air passages and a pharmaceutically acceptable carrier.

10. The pharmaceutical composition according to claim 9, wherein said second therapeutic agent for the treatment of obstructive diseases of the air passages is selected from the group consisting of a $\beta_2$-sympathomimetic and atrial natriuretic peptide.

11. The pharmaceutical composition according to claim 10, wherein said $\beta_2$-sympathomimetic is selected from the group consisting of fenoterol, salbutamol and terbutalin.

* * * * *